US00PP23976P2

(12) United States Plant Patent
Tsukahara

(10) Patent No.: US PP23,976 P2
(45) Date of Patent: Oct. 8, 2013

(54) CALIBRACHOA PLANY NAMED 'CCZLA02-0'

(50) Latin Name: ***Calibrachoa* sp.**
Varietal Denomination: CCZLA02-0

(75) Inventor: Jun Tsukahara, Yame (JP)

(73) Assignee: Daiichi Engei Co. Ltd. (JP)

( * ) Notice: Subject to any disclaimer, the term of this patent is extended or adjusted under 35 U.S.C. 154(b) by 0 days.

(21) Appl. No.: 13/385,493

(22) Filed: Feb. 21, 2012

(51) Int. Cl.
*A01H 5/00* (2006.01)

(52) U.S. Cl.
USPC ..... Plt./413

(58) Field of Classification Search
USPC ..... Plt./413
See application file for complete search history.

*Primary Examiner* — Kent L Bell

(57) ABSTRACT

A new and distinct *Calibrachoa* cultivar named 'CCZLA02-0' is disclosed, characterized by large flowers of a purple color with a yellow center. The new variety is a *Calibrachoa*, normally produced as an ornamental outdoor garden or container plant.

2 Drawing Sheets

Latin name of the genus and species: *Calibrachoa* sp.
Variety denomination: 'CCZLA02-0'.

BACKGROUND OF THE INVENTION

The new *Calibrachoa* cultivar is a product of a planned breeding program conducted by the inventor, Jun Tsukahara in Yame, Fukuoka, Japan The objective of the breeding program was to produce new *Calibrachoa* varieties for commercial ornamental applications. The cross resulting in this new variety was made during September 2007.

The seed parent is an unpatented, unnamed proprietary seedling variety of *Calibrachoa* with a light purple flower. The pollen parent is an unpatented, unnamed proprietary seedling variety of *Calibrachoa* with a bright purple flower. The new variety was discovered in May, 2008 by the inventor in a group of seedlings resulting from the 2007 crossing, in a research greenhouse in Yame, Fukuoka, Japan.

Asexual reproduction of the new cultivar 'CCZLA02-0' by tissue culture was first performed at a research laboratory in Yame, Fukuoka, Japan in May, 2008. Subsequently, the new variety has been propagated by vegetative cuttings, and has shown that the unique features of this cultivar are stable and reproduced true to type in successive generations.

SUMMARY OF THE INVENTION

The cultivar 'CCZLA02-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CCZLA02-0'. These characteristics in combination distinguish 'CCZLA02-0' as a new and distinct *Calibrachoa* cultivar:

1. Large flower size
2. Clear purple flower with a yellow center
3. Trailing plant habit

PARENT COMPARISON

Plants of the new cultivar 'CCZLA02-0' are similar to plants of the seed parent, an unpatented, unnamed proprietary seedling variety of *Calibrachoa* with a light purple flower, in most horticultural characteristics, however, plants of the new cultivar 'CCZLA02-0' produce larger flowers. Additionally, plants of the new cultivar are less trailing, with shorter stems and wider leaves than the seed parent.

Plants of the new cultivar 'CCZLA02-0' are similar to plants of the pollen parent, an unpatented, unnamed proprietary seedling variety of *Calibrachoa* with a bright purple flower, in most horticultural characteristics, however, plants of the new cultivar 'CCZLA02-0' produce a lighter colored flower. Additionally, plants of the new cultivar are more trailing, with longer stems than the pollen parent

COMMERCIAL COMPARISON

Plants of the new cultivar 'CCZLA02-0' are best compared to the variety *Calibrachoa* 'SUNbel kopachip' U.S. Plant Pat. No. 20,092. The two *Calibrachoa* varieties are similar in most horticultural characteristics, however the new variety has larger flowers of a lighter purple flower color.

BRIEF DESCRIPTION OF THE PHOTOGRAPHS

Figure 1:
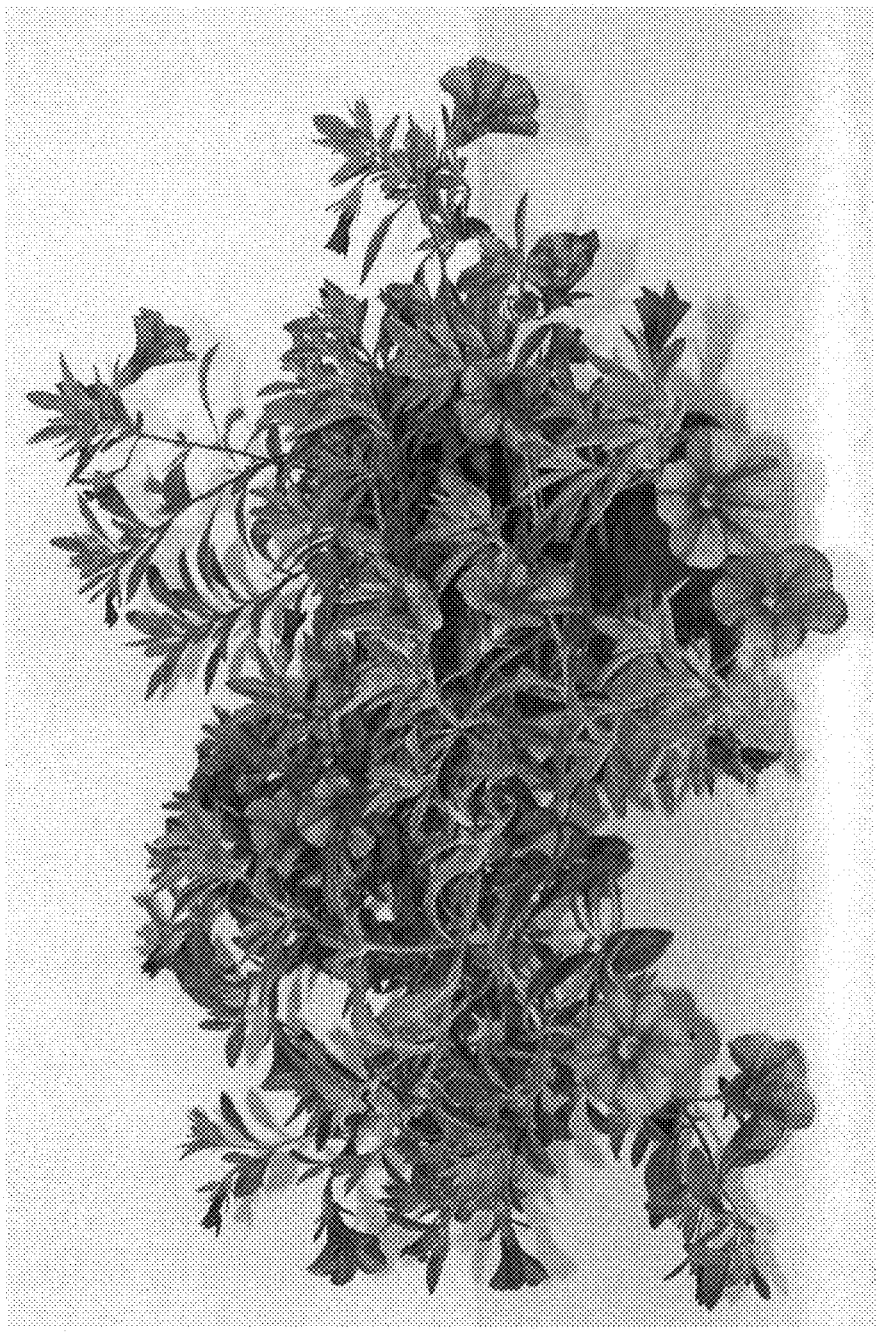
Figure 2:
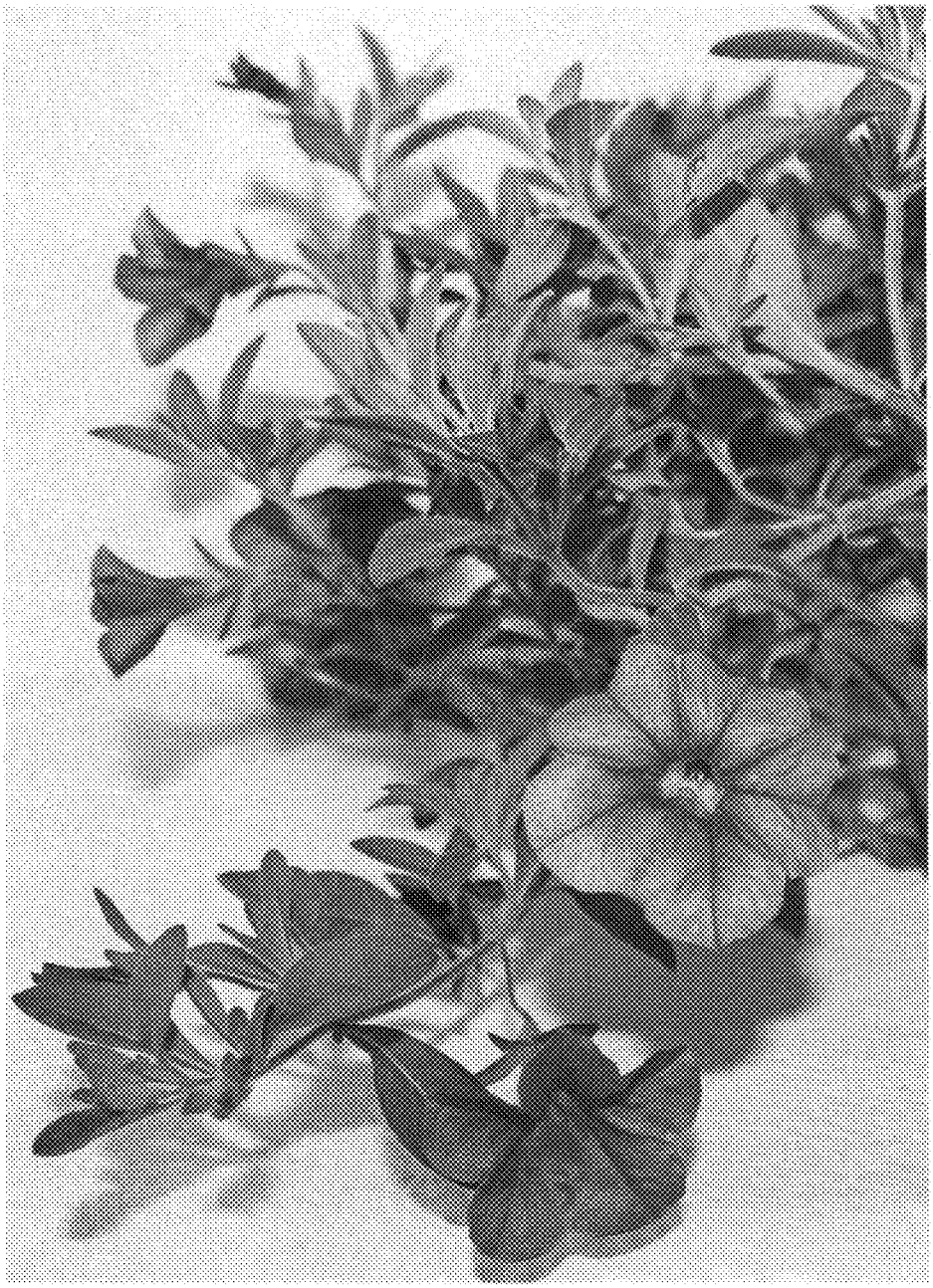

The accompanying photograph in FIG. 1 illustrates in full color a typical plant of 'CCZLA02-0' grown in a greenhouse, in a 6 inch pot. FIG. 2 illustrates in full color a close up of a typical bloom. Age of the plant photographed is approximately 4 months from 5 rooted cuttings. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'CCZLA02-0' plants grown in a commercial greenhouse in Oxnard, Calif. The growing temperature ranged from 18° C. to 25° C. The greenhouse is subject to partial shade. General light conditions are bright, normal sunlight with some shade during the brightest part of the day. Measurements and numerical values represent averages of typical plant types.

Botanical classification: *Calibrachoa* sp. 'CCZLA02-0'.

PROPAGATION

Time to initiate roots: About 10 to 12 days at approximately 25° C.

Root description: Fine, fibrous.

PLANT

Growth habit: Trailing.

Pot size of plant described: 6 inch.

Age of plant described: Approximately 4 months from 5 rooted cuttings.

Height: Approximately 16 cm.

Plant spread: approximately 48 cm.

Growth rate: Rapid.

Branching characteristics: Moderately free branching.

Length of primary lateral branches: Approximately 21 cm.

Diameter of lateral branches: Approximately 0.2 cm.

Quantity of primary lateral branches: Approximately 20.

Characteristics of primary lateral branches:

- *Form*.—Round.
- *Color*.—Near RHS Yellow-Green 143C, moderately flushed Greyed-Purple 187A.
- *Texture*.—Pubescent.
- *Strength*.—Strong.

Internode length: Average 1.5 cm.

FOLIAGE

Leaf:

- *Arrangement*.—Opposite.
- *Quantity*.—Approximately 20 per lateral branch.
- *Average length*.—Average 4.5 cm.
- *Average width*.—Average 1.1 cm.
- *Shape of blade*.—Oblanceolate.
- *Apex*.—Broadly acute to obtuse, some leaves without acute tip.
- *Base*.—Acuminate.
- *Margin*.—Entire.
- *Texture of surfaces*.—Slightly pubescent.
- *Angle of attachment*.—75°.
- *Aspect*.—Flat.
- *Color*.—Young foliage upper side: Near RHS Green 143B. Young foliage under side: Near RHS Green 137C. Mature foliage upper side: Near RHS Green 143A. Mature foliage under side: Near RHS Green 138A.
- *Venation*.—Type: Pinnate. Venation color upper side: Near RHS Yellow-Green 144B. Venation color under side: Near RHS Yellow-Green 145A.
- *Petiole*.—Not Present.

FLOWER

Natural flowering season: All year round in moderate climates.

Days to flowering from rooted cutting: Approximately 4 weeks.

Inflorescence and flower type and habit: Terminal, Single, Salverform.

Rate of flower opening: 1 to 3 days from bud to fully opened flower.

Flower longevity on plant: About 3 to 6 days.

Approximate quantity of flowers per plant: 30-40 at 60 days old.

Persistent or self-cleaning: Self-cleaning.

Fragrance: Faint.

Bud:

- *Shape*.—Tubular.
- *Length*.—1.7 cm.
- *Diameter*.—0.5 cm.
- *Color*.—At proximal end Near RHS Yellow-Green 145A. At distal end Near RHS Violet 83C.

Flower size:

- *Diameter*.—Average 3.2 to 4.5 cm.
- *Length*.—Average 3.5 cm.
- *Flower tube diameter at distal end*.—Average 1.2 cm.
- *Flower tube diameter at proximal end*.—0.4 cm.

Petals:

- *Length from throat*.—Average 2.2 cm.
- *Width*.—Average 1.8 cm.
- *Quantity*.—5 fused petals.
- *Texture*.—Smooth.
- *Apex*.—Acute.
- *Margin*.—Entire.
- *Color*.—When opening: Inner surface: Near RHS Violet 83A, veins Purple 78A. Outer surface: Near RHS Violet 83B, veins Purple 79A. Fully opened: Inner surface: Near RHS Violet 83A, veins Purple 78A. Outer surface: Near RHS Purple-Violet N81C, veins Purple 79B. Flower throat (inside): Base Near RHS Yellow 9 C, White N155A near top of throat. Flower throat, vein: Near RHS Greyed-Purple N186B. Flower tube (outside): Near RHS Yellow-Green 150C. Flower tube, vein: Near RHS Purple N79A. Petal color, fading to: Near RHS Violet-Blue N92A.

Calyx/sepals:

- *Quantity per flower*.—5.
- *Shape*.—Lanceolate.
- *Length*.—Approximately 1.5 cm.
- *Width*.—Approximately 0.4 cm.
- *Apex*.—Acute.
- *Base*.—Fused.
- *Margin*.—Entire.
- *Texture*.—Pubescent.
- *Color*.—Upper Surface: Near RHS Green 143A. Lower Surface: Near RHS Yellow-Green 146A.

Peduncle:

- *Length*.—Average 2.1 cm.
- *Diameter*.—0.1 cm.

*Texture*.—Pubescent.

*Color*.—Near RHS Yellow-Green 144A, flushed Greyed-Purple N186B.

*Orientation*.—Straight or slight undulation, 45° angle from stem.

REPRODUCTIVE ORGANS

Stamens:

*Number*.—5.

*Filament length*.—0.7 cm.

Anthers:

*Length*.—0.1 cm.

*Shape*.—Round.

*Color*.—Near RHS Yellow 9A.

*Pollen*.—Color: Near RHS Yellow 12A. Quantity: Moderate.

Pistil:

*Number:* 1.

*Length*.—0.8 cm.

*Style*.—Length: 0.7 cm. Color: Near RHS Yellow-Green 144C.

*Stigma*.—Shape: Bilobed. Color: Near RHS Green 143B. Ovary Color: Near RHS Green 143B.

OTHER CHARACTERISTICS

Seeds and fruits: Not observed.

Disease/pest resistance: Neither resistance nor susceptibility to pathogens and pests common to *Calibrachoa* have been observed.

Temperature tolerance: The new variety tolerates temperatures between 0 to 40° C.

What is claimed is:

1. A new and distinct cultivar of *Calibrachoa* plant named 'CCZLA02-0' as herein illustrated and described.

* * * * *